(12) United States Patent
Sadler et al.

(10) Patent No.: US 6,699,258 B1
(45) Date of Patent: Mar. 2, 2004

(54) STERILIZATION AND LIGATION CLIPS

(75) Inventors: Kenneth George Sadler, West Sussex (GB); John Darren Giddins, Nottingham (GB)

(73) Assignee: Femcare (Cyprus) Limited, Limassol (CY)

( * ) Notice: Subject to any disclaimer, the term of this patent is extended or adjusted under 35 U.S.C. 154(b) by 0 days.

(21) Appl. No.: 10/130,053
(22) PCT Filed: Nov. 17, 2000
(86) PCT No.: PCT/GB00/04390
§ 371 (c)(1), (2), (4) Date: May 14, 2002
(87) PCT Pub. No.: WO01/35836
PCT Pub. Date: May 25, 2001

(30) Foreign Application Priority Data

Nov. 17, 1999 (GB) .............................................. 9927040

(51) Int. Cl.⁷ ................................................ A61B 17/00
(52) U.S. Cl. ...................................................... 606/157
(58) Field of Search ................................. 606/151, 157, 606/143, 144, 147, 219, 221, 205, 206, 207

(56) References Cited

U.S. PATENT DOCUMENTS

| 4,489,725 A | 12/1984 | Casey et al. |
| 4,702,247 A | 10/1987 | Blake, III et al. |
| 5,002,552 A | 3/1991 | Casey |
| 5,849,019 A | 12/1998 | Yoon |

FOREIGN PATENT DOCUMENTS

| GB | 1530282 | 10/1978 |
| GB | 2177748 | 1/1987 |
| GB | 2226958 | 7/1990 |
| GB | 2251794 | 7/1992 |
| GB | 2297487 | 8/1996 |
| WO | WO 01 05309 | 1/2001 |

Primary Examiner—Kevin T. Truong
(74) Attorney, Agent, or Firm—Salter & Michaelson

(57) ABSTRACT

A medical clip (10) comprising upper and lower jaws and adapted to be latched by latching of the upper jaw (14) against the lower jaw (12) in which the upper jaw (14) is provided with stress relief means.

18 Claims, 5 Drawing Sheets

STERILIZATION AND LIGATION CLIPS

TECHNICAL FIELD

The present invention relates to medical clips and more particularly to sterilisation or ligation clips suitable for occluding blood vessels.

BACKGROUND OF RELATED ART

Known clips are made from metal upper and lower jaws hinged together, the jaws being hinged to allow the jaws to be opened to encompass a tube or blood vessel. Usually the jaws are provided with silicon rubber lining. The clip is closed by deformation of the upper jaw which is curved, the deformation lengthening the upper jaw which is then latched under a latch on the lower jaw. Such a clip is described in U.S. Pat. No. 4,489,725 (FILSHIE).

A problem with such clips is that when made of a material such as titanium, the upper jaw or gate is work hardened when initially deformed into the curved shape.

The consequence of the work hardening of the upper jaw material is that it requires greater force to overcome the resistance in the material caused by such work hardening than is necessary to close the tube or blood vessel structures occluded or ligated by the clip.

This can result in one of two possible malfunctions of the clip.

Firstly, the clip can fail to close even if the correct closure pressure is applied because the upper jaw can spring back because additional strength is required to fully lengthen the upper jaw. The clip therefore fails.

The second condition is that sufficient strength is applied to straighten the upper jaw, but this force has to be greater than is required to occlude or ligate. In this case the tube or blood vessel can be severed creating a possible emergency situation.

SUMMARY

It is an object of the present invention to provide a clip which obviates the above problem.

The present invention, therefore, provides a medical clip comprising elongate upper and lower jaws at least said upper jaw being metallic, said lower jaw being hinged by connection to said upper jaw at a first end of said elongate structure and said lower jaw being formed with latch means at said other end, said upper jaw being formed curved in a non operated condition and said upper jaw being constructed to be deformable under applied load to thereby extend the effective length of said upper jaw to enable said upper jaw to latch under said latch means in said lower jaw when in an operated condition and in which said upper elongate jaw is provided with stress relief means in an intermediate area along said length of said upper jaw.

Preferably, said stress relief means comprises a hole extending through said upper jaw.

Preferably, both said upper and lower jaws are metallic.

In a preferred embodiment at least one of said jaws is lined internally with a silicone rubber lining.

More preferably, both said jaws are internally lined with a silicone rubber lining.

In a specific embodiment said upper jaw comprises a first substantially straight portion situated at said first end nearest to said hinge, a second curved portion and a third substantially straight portion, said third portion providing a latching surface for engagement with said lower jaw and in which said hole is formed in said second curved portion.

In a preferred embodiment, the second curved portion comprises a complex curvature, including two sections of different radii of curvature.

BRIEF DESCRIPTION OF THE DRAWINGS

Embodiment of the present invention will now be described, by way of example with reference to the accompanying drawings in which.

DETAILED DESCRIPTION OF THE ILLUSTRATIVE EMBODIMENTS

Figure 1:
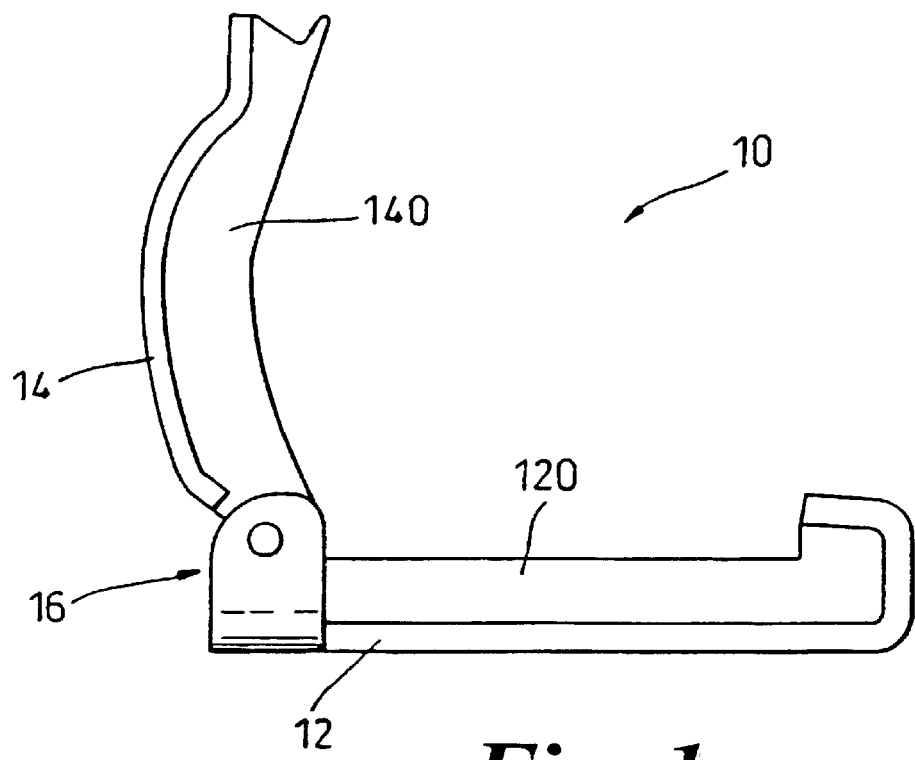
FIG. 1 shows a clip according to the present invention in side elevation.

With reference now to FIG. 1, the drawings of the medical clip 10 comprises a lower jaw 12 and an upper jaw 14 which are connected by a suitable hinge structure 16.

In this embodiment both upper and lower jaws are provided with respective silicone rubber linings 140, 120.

Figure 3:
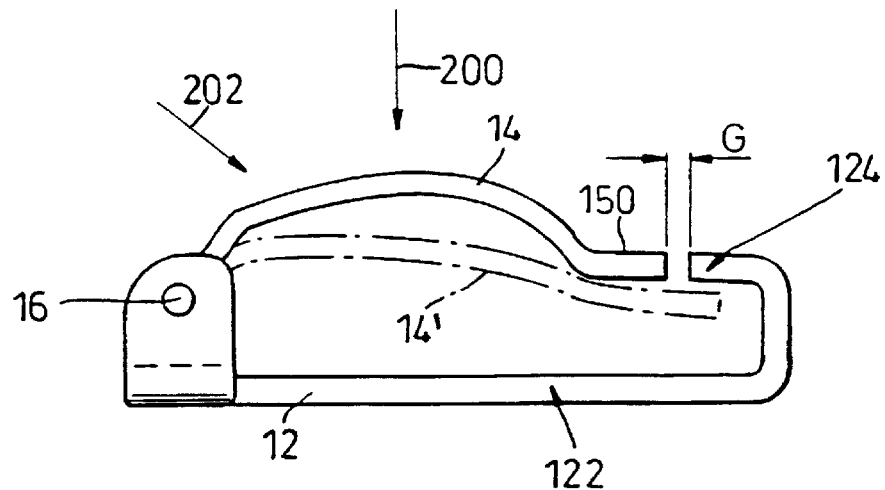
FIG. 3 shows the clip of FIG. 1 with the silicon rubber lining removed.
Figure 4:
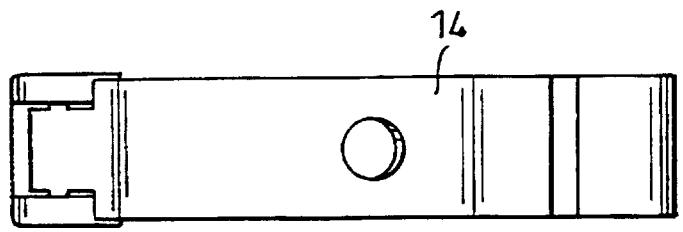
FIG. 4 shows the clip of FIG. 3 in plan view.
Figure 5:
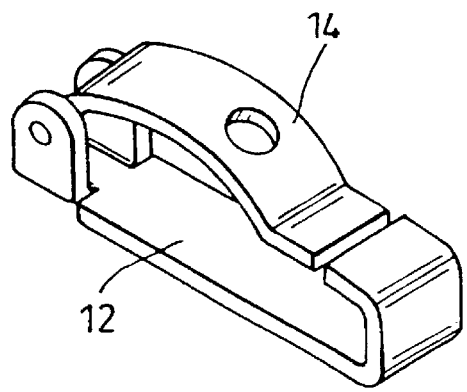
FIG. 5 shows the clip of FIG. 4 in perspective view.

With reference to FIG. 3 the clip shown in FIG. 1 is shown without the silicon rubber linings to illustrate the upper and lower jaw structure.

The lower jaw 12 comprises a generally flat elongate section 122 and a latch portion 124 formed by bending the lower jaw.

Figure 6:
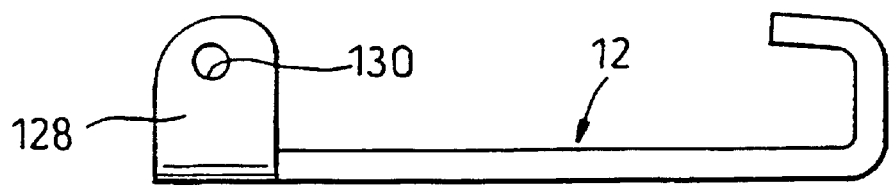
FIG. 6 shows the lower jaw of the clip in FIG. 3 in side elevation.
Figure 7:
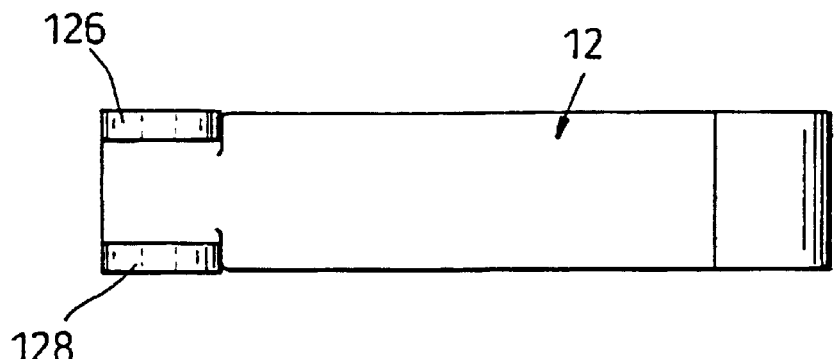
FIG. 7 shows the lower jaw in plan view.
Figure 8:
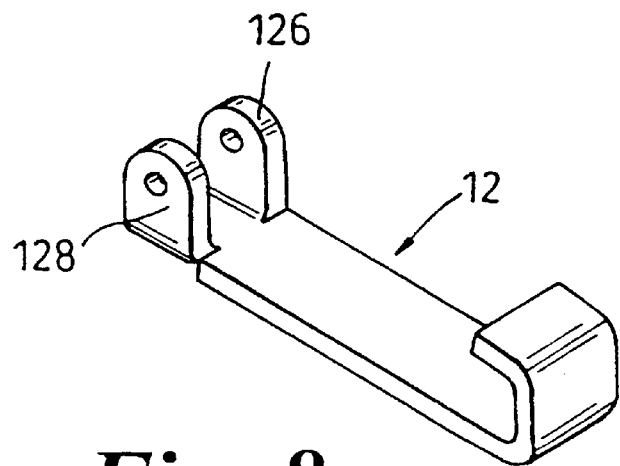
FIG. 8 shows the lower jaw in a perspective view.

The lower jaw comprises two upturned lugs 126, 128 (FIG. 7) which are provided with holes 130, 132 (only 130 being shown in FIG. 6) which receive hinge pins 142, 144 (FIG. 11) found on the upper jaw 14.

The hinge mechanism may be formed by other means not shown and is not a critical feature of the present invention.

Figure 9:
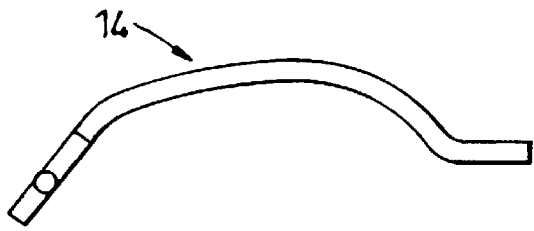
FIG. 9 shows the upper jaw of the clip of FIG. 3 in side elevation.
Figure 10:
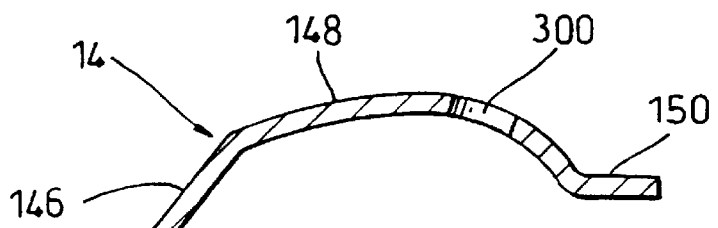
FIG. 10 shows the upper jaw of FIG. 9 in longitudinal cross section.
Figure 11:
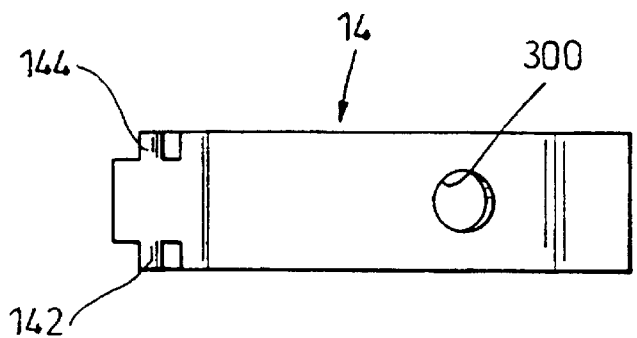
FIG. 11 shows the upper jaw of FIG. 9 in plan view.

The upper jaw 14 shown in greater detail in FIGS. 9 to 11, comprises a generally curved elongate structure including a first generally straight section 146, a second generally arcuate section 148, and a third generally straight section 150.

As seen in FIG. 3, section 150 of upper jaw 14 is designed to engage under latch member 124 of lower jaw 12 when upper jaw 14 is straightened by application of force in the direction of arrow 200 which causes the upper jaw 14 to be permanently deformed (straightened) as indicated by dotted line 14'.

As can be seen initially the upper and lower jaws are proportioned such that a defined gap G is present in the non operated condition. This gap ensures that the clip can be closed from the position shown in FIG. 1 to the position shown in FIG. 3 without straightening of the upper jaw.

Further movement of the upper jaw in the direction of arrow 200 or 202 dependent on the apparatus used for the closure of the clip (see also co-pending UK patent application No 9919170.2 multiple application) will cause the upper jaw to be straightened to the position shown at 14' in which the section 150 is forced under the latch 124 thereby permanently closing the clip.

However, if the upper jaw 14 has been work hardened during formation of the profile of the upper jaw, the force required in the direction of arrow 200, 202 will be greater than that required if no work hardening has taken place.

This creates two problems, firstly, if not enough force is applied in the direction of arrow 200 the clip will not latch correctly because the upper jaw 14 will not have been elongated sufficiently to overcome the gap G. The upper jaw because it may have a spring memory may therefore spring back and cause the clip to unlatch even though it appeared to have been properly latched. Under these circumstances, the clip will therefore spring open, possibly not immediately dependent on the amount of latching.

Secondly, if too much force is applied in the direction of arrow 200, 202 then even though the jaws are silicon lined the force applied to the structure to be occluded or ligated may be such as to damage or completely sever the structure.

Since the clip will possibly still be attached to one part of the structure the consequences in keyhole type surgery can result in emergency surgery being necessary to remove the clip and repair any damage.

In accordance with the present invention the necessity to apply excessive force is avoided by providing stress relief means in the upper jaw.

Figure 2:
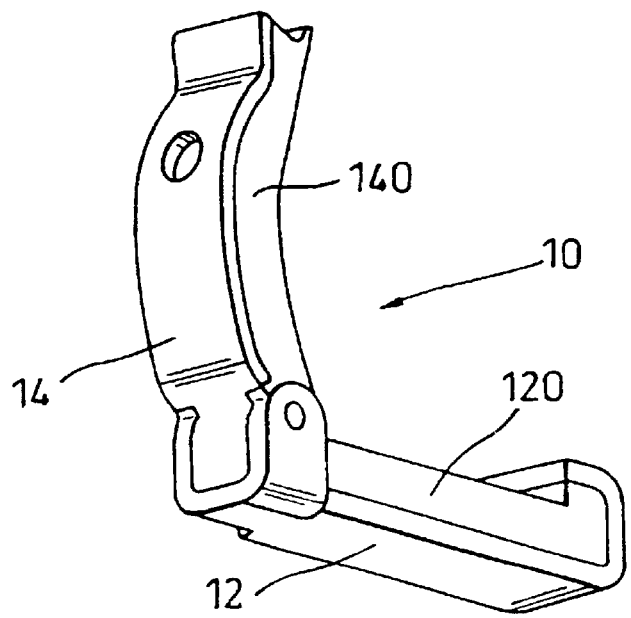
FIG. 2 shows a perspective view of the clip of FIG. 1.

The stress relief in the example shown in FIGS. 10 and 11 (see also FIG. 2) comprises a hole 300 formed through the upper jaw. In this example the hole diameter is approximately half the thickness of the width of the upper jaw.

The size of the hole can be varied to alter the degree of weakening or stress relief. Alternatively, a lateral groove could be formed in the material of the upper jaw to provide the required stress relief. The depth of the groove can be adjusted to vary the stress relief. In a specific example a groove of depth 0.1 mm in an upper jaw for having a depth of 0.65 mm has been found to be effective. Additionally, the position of the hole and/or groove can be varied to alter the characteristics of the upper jaw.

The stress relief could comprise other means such as, for example, an oval hole punched out when the upper jaw curvature is being created.

The stress relief assists in the straightening of the upper jaw to thereby ensure that correct latching of the clip occurs without the use of excessive force applied in the direction of arrow 200.

The upper jaw strength is still sufficient to ensure that the clip remains latched. The use of a central hole provides pressure on the edges of the clip and thereby ensures effective closing pressure on the structure to be occluded or ligated.

A further possible advantage in the provision of the hole is that it is possible to injection mould the silicone lining through the hole.

A similar hole could be provided in the lower jaw to allow similar moulding procedures with the lower jaw.

Figure 9A:
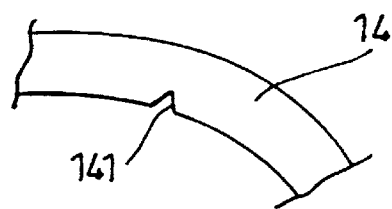
FIG. 9a shows a portion of the upper jaw of the clip illustrating an alternative form of stress relief.

In a further embodiment illustrated in FIG. 9a the stress relief means comprises a notch 141 formed in the upper jaw or gate of the clip. The notch 141 may be formed by filing or by stamping which may conveniently be carried out simultaneously with the curving of the upper jaw.

The size of the notch may be varied to regulate the stress relief depending on the thickness and length of the upper jaw.

The following compression tests were carried out on practice clip designs.

Compression was applied to the peak of the gate of the clips and the compression distance measured starting 7 mm above the base of the tester and continuing to 3 mm above the base, when the tester was released incrementally until contact with the clip was lost, measuring the force at a series of points.

Various dimensional checks were made before compression. The final length of the gate after compression was also measured.

These tests were carried out on the two clips used for the (non-destructive) hardness test. A design modification to weaken a further clip with 0.65 mm gate was then applied and this was tested.

Results:

| Clip description | No 47, 0.5 mm gate | 0.65 gate as built | 0.65 gate, weakened by filing, between centre of gate and latch |
| --- | --- | --- | --- |
| Initial gate length measured vertically from base (mm) | 14.26 | 14.28 | 14.20 |
| Final gate length measured in closed clip (mm) | 13.71 | 13.71 | 13.99 |
| Max force, at compression to 3 mm (N) | 54 | 88 | 82 |
| Relaxation of force with time at compression to 3 mm, approx. (N) | 6 | 8 | 8 |
| Springback of centre of gate after removal of force (mm) | 0.75 | 0.75 | 0.75 |
| Closed clip height at centre (mm) | 3.8 | 3.78 | 3.8 |

The weakened clip had the shortest initial and the longest final gate length. This would be expected to lead to much more reliable closure.

The closure force on the 0.5 mm gate Ligation clip is similar to that for a Filshie clip—54 N compared to 88 N. This could be useful if it is wished to reduce the force to suite applicator design or the "feel" to the surgeon.

The closure force on the weakened clip was by comparison much nearer to the unweakened clip—82 N compared to 88 N. The closure force may prove a useful design and production measure of the amount of weakening applied.

For clips with holes in the upper jaw the following results were observed.

Tests were carried out on samples of Ligation Clip with 0.5 mm thick gate, using the compression tester, without silicone rubber samples in the clips.

Figure 12:
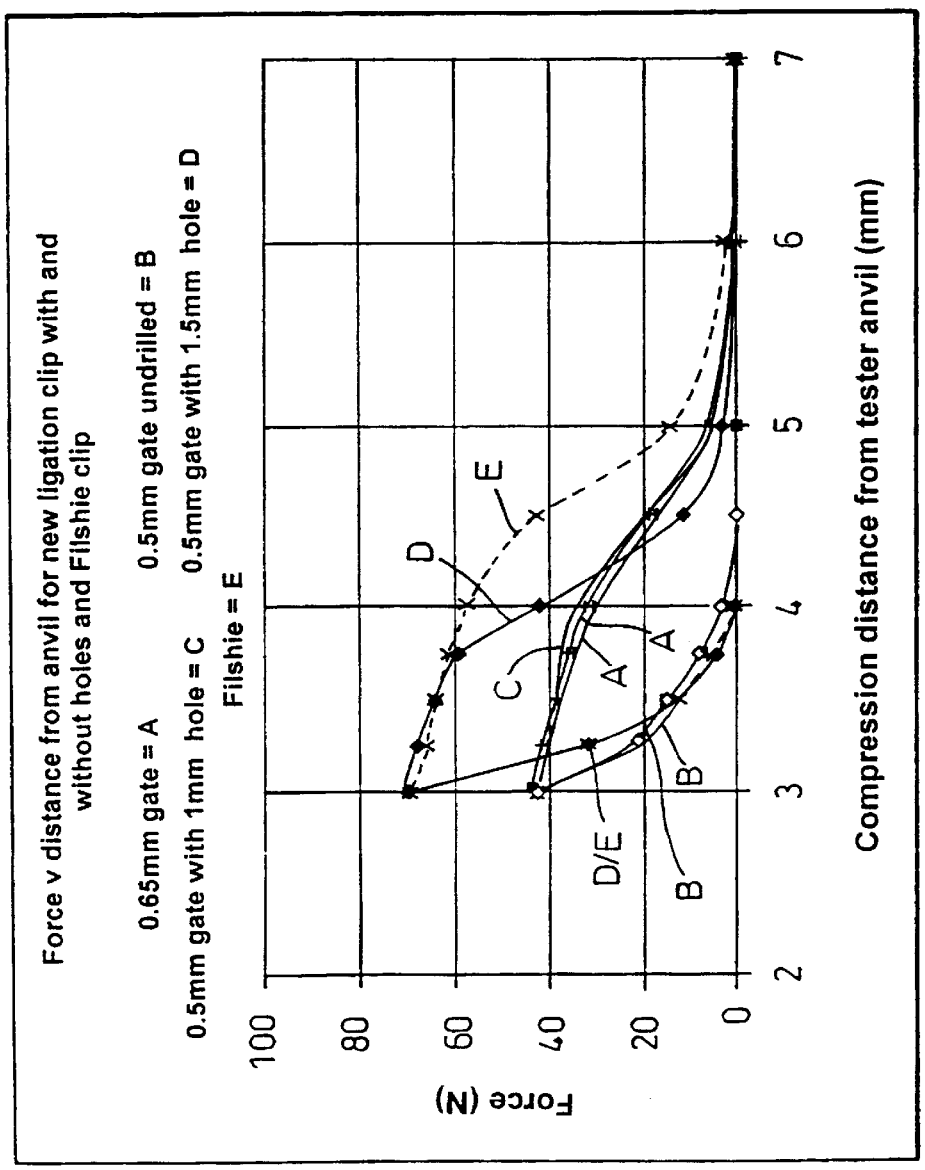
FIG. 12 shows a series of hysterisis graphs of force-v-distance from anvil for a ligation clip according to the present invention with and without holes and for a Filshie clip. Hysterisis curve A is for a 0.65 mm gate; hysterisis curve B is a 0.5 mm undrilled gate; hysterisis curve C is for a 0.5 mm gate with a 1 mm hole; hysterisis curve D is a 0.5 mm hole and hysterisis curve E is for the known Filshie sterilisation clip.

The tests were carried out and the results compared to earlier tests done on Filshie clips and new undrilled Ligation clips with 0.65 and 0.5 mm gates with the object of establishing the effect of the holes on closure force. All these results are shown in the chart shown in FIG. 12.

The results show that the holes do not generally affect the closure force. The results for 1 mm hole show very slightly more force than for the 1.5 mm hole, as might be expected, but the differences are negligible and very similar to that for the clips with undrilled 0.5 mm gate.

The weakening of the clip at a point about 5 mm from the latch end of the gate increases the latching effectiveness, and the clips tested here latched well.

These holes, negligibly affect the closure force. This result is consistent with the fact that the hole is in a part of the clip which is deliberately formed at a steep angle to the applied force (which is vertically onto the crest of the clip) and may be attributed to the yield 1o occurring over a considerable part of the length of the gate, which is what is needed for the maximum gate extension and optimum latching. This, if repeatable, is a highly desirable outcome.

What is claimed is:

1. A medical clip comprising:
   an upper jaw having a first end and a second end opposite the first end;
   a lower jaw having:
     a.) a first end and a second end opposite the first end;
     b.) an elongate section extending from said first end;
     c.) a latch portion disposed at said second end;
       said first end of said upper jaw being hingedly connected to said first end of said lower jaw;
   a stress relief disposed in said upper jaw in an intermediate area between said first end and said second end of said upper jaw; and
   wherein said upper jaw has a first curvature in a nonoperated position and wherein said upper jaw is constructed and arranged to be permanently deformable under an applied load such that said first curvature is reduced allowing said second end of said upper jaw to latch with said latch portion of said lower jaw in an operated position.

2. A medical slip as claimed in claim 1, wherein said stress relief comprises a hole extending through said upper jaw.

3. A medical clip as claimed in claim 2, wherein said upper jaw includes a first substantially straight portion situated at said first end nearest to said hinge, a second curved portion and a third substantially straight portion, said third portion providing a latching surface constructed and arranged to engage said lower jaw, and wherein said hole is formed in said second curved portion.

4. A medical clip as claimed in claim 3, wherein said second curved portion comprises a complex curvature, including two sections of different radii of curvature.

5. A medical clip as claimed in claim 4, wherein said hole has a diameter approximately half of the width of said upper jaw.

6. A medical clip as claimed in claim 1, wherein at least one of said upper and lower jaws are metallic.

7. A medical clip as claimed in claim 1, wherein at least one of said upper and lower jaws is lined internally with a silicone rubber lining.

8. A medical clip as claimed in claim 1, wherein both said upper and lower jaws are internally linked with a silicone rubber lining.

9. A medical clip as claimed in claim 1, wherein said stress relief comprises a groove formed in said upper jaw.

10. A medical clip comprising:
    an upper jaw having a first end and a second end opposite the first end;
    a lower jaw having:
      a.) a first end and a second end opposite the first end;
      b.) an elongate section extending from said first end;
      c.) a latch portion disposed at said second end;
        said first end of said upper jaw being hingedly connected to said first end of said lower jaw;
    a stress relief means disposed in said upper jaw in an intermediate area between said first end and said second end of said upper jaw; and
    wherein said upper jaw has a first curvature in a nonoperated position and wherein said upper jaw is constructed and arranged to be deformable under an applied load such that said first curvature is reduced allowing said second end of said upper jaw to latch with said latch portion of said lower jaw in an operated position.

11. A medical slip as claimed in claim 10, wherein said stress relief means comprises a hole extending through said upper jaw.

12. A medical clip as claimed in claim 11, wherein said upper jaw includes a first substantially straight portion situated at said first end nearest to said hinge, a second curved portion and a third substantially straight portion, said third portion providing a latching surface constructed and arranged to engage said lower jaw, and wherein said hole is formed in said second curved portion.

13. A medical clip as claimed in claim 12, wherein said second curved portion comprises a complex curvature, including two sections of different radii of curvature.

14. A medical clip as claimed in claim 13, wherein said hole has a diameter approximately half of the width of said upper jaw.

15. A medical clip as claimed in claim 10, wherein said stress relief means comprises a groove formed in said upper jaw.

16. A medical clip as claimed in claim 10, wherein at least one of said upper and lower jaws are metallic.

17. A medical clip as claimed in claim 10, wherein at least one of said upper and lower jaws is lined internally with a silicone rubber lining.

18. A medical clip as claimed in claim 10, wherein both said upper and lower jaws are internally linked with a silicone rubber lining.

* * * * *